United States Patent [19]
Narayan

[11] Patent Number: 5,258,417
[45] Date of Patent: Nov. 2, 1993

[54] LOW VISCOSITY POLYMERIC MDI

[75] Inventor: Thirumurti Narayan, Grosse Ile, Mich.

[73] Assignee: BASF Corporation, Parsippany, N.J.

[21] Appl. No.: 997,005

[22] Filed: Dec. 28, 1992

[51] Int. Cl.$^5$ .............................................. C08G 18/14
[52] U.S. Cl. ..................................... 521/160; 528/67; 252/182.21
[58] Field of Search .......................... 521/160; 528/67; 252/182.21

[56] References Cited
U.S. PATENT DOCUMENTS 4,256,849  3/1981  Ick et al. .............................. 521/129

Primary Examiner—Maurice J. Welsh
Attorney, Agent, or Firm—William G. Conger

[57] ABSTRACT

The present invention deals with a polymethylene polyphenylisocyanate blend having a viscosity range of from 15 to 37 cps at 25° C. Specifically, the blend is prepared by mixing a polymethylene polyphenylisocyanate with monomeric diphenylmethane diisocyanate. The unique characteristics of this product are that it displays good storage stability under ambient conditions and has a low viscosity. It is useful in the production of polyurethane foams and adhesives.

5 Claims, No Drawings

LOW VISCOSITY POLYMERIC MDI

BACKGROUND OF THE INVENTION

Polyisocyanate mixtures containing diphenylmethane diisocyanates (MDI) and higher functional polymethylene polyphenylpolyisocyanates (polymeric or crude MDI) are known. For example, the general synthesis product of the phosgenation of polyphenyl amines yields, depending upon conditions such as catalyst type, temperature and the like, a mixture of oligomers and isomers. U.S. Pat. No. 3,344,162 describes the production of aromatic polyisocyanates containing from about 50 to about 95 percent by weight of the diisocyanate of which from about 10 percent to about 95 percent by weight is the 2,4'-isomer. U.S. Pat. No. 3,362,979 claims a mixture of polyisocyanates containing from 20 percent to 100 percent of the diisocyanates of which 20 percent to 95 percent by weight is the 2,4'-isomer. U.S. Pat. No. 3,960,788 describes a mixture of polymethylene polyphenylpolyisocyanates having an average functionality of about 2.1 to about 2.4 of from about 60 percent to 75 percent by weight MDI and from 25 percent to about 40 percent higher functional polymethylene polyphenylisocyanates. The diphenylmethane diisocyanate has an isomer content of about 60 percent to about 80 percent 4,4'-isomer, about 18 percent to about 33 percent 2,4'-isomer, and about 2 percent to 7 percent 2,2'-isomer. These synthesis mixtures are disclosed as having a viscosity of about 60 cps at 25° C. U.S. Pat. No. 4,256,849 claims a process for the production of cold setting flexible foams wherein a mixture of diphenylmethane diisocyanates and polyphenylpolymethylene polyisocyanates containing from 60 to 90 percent by weight of 4,4'-diphenylmethane diisocyanate and from 3 to 30 percent by weight of 2,4'-diphenylmethane diisocyanate is used. It further discloses the amount of polyphenylpolymethylene polyisocyanates to be from 0 to 37 percent by weight. Unfortunately, the synthesis mixtures having a high content (50 percent to 100 percent by weight) of the 2-ring MDI isomer, where the major isomer is 4,4'-, tend to form insoluble crystal dimers in solution. The product, in turn, must then be filtered to remove the unreactive solids.

SUMMARY OF THE INVENTION

It has unexpectedly been found that storage stable blends of polymethylene polyphenylpolyisocyanates having viscosities from 15 to 37 cps may be prepared by adding diphenylmethane diisocyanates to the polymeric MDI in amounts such that the two-ring isomer content does not exceed 80 percent by weight of the blend. Based on the above limitation, the ring distribution of the blend is as follows:

1. from 60 percent to about 75 percent by weight 4,4'-diphenylmethane diisocyanate,
2. from 4 percent to about 10 percent by weight 2,4-diphenylmethane diisocyanate,
3. less than 1 percent by weight 2,2'-diphenylmethane diisocyanate,
4. from 8 percent to about 15 percent by weight of a 3-ring polymethylene polyphenylpolyisocyanate, and,
5. from 5 percent to about 15 percent by weight of a 4-ring and higher oligomeric polymethylene polyphenylpolyisocyanate.

While it is possible to have storage stable low viscosity blends having greater than 80 percent by weight 2-ring content, to do so requires adding greater than 10 percent by weight of the 2,4'-isomer of MDI and uretonimine-modified MDI. This is not desired, as the object is to prepare a polymeric MDI blend wherein said blend has as high a 2-ring content as possible while maintaining the desired physical characteristics and to maximize the ratio of 4,4'- to 2,4'-MDI.

The low viscosity isocyanates of the present invention offer advantages in processing and finished product performance. The low viscosity provides for ease in handling and processing in various formulations, e.g., polyurethane adhesive and microcellular foam formulations. Its stability allows processing at temperatures of between 20° C. and 35° C. while giving the advantages of a high pure (4,4'-) content MDI. High resilient foams using the low viscosity isocyanates of the present invention have shown up to a 20 percent increase in tear strength. The isocyanate of the present invention may, of course, be used in the preparation of prepolymers.

The polymeric MDI and pure isomeric MDI used in the present invention are prepared by conventional means known in the art. The reaction of amines with phosgene (phosgenation) has been used almost exclusively for the manufacture of isocyanates. The details of processing vary with the specific isocyanate and in particular for aromatic and aliphatic isocyanates, but the general approach is the same. In general, the manufacturing process for aromatic isocyanates have the following approach: the solution of an amine in an aromatic solvent, such as xylene, mono-dichlorobenzene, or o-dichlorobenzene is mixed with a solution of phosgene in the same solvent at a temperature below 60° C. The resulting mixture slurry is digested in one to three stages for several hours at progressively increasing temperatures up to 200° C. and is accompanied by the injection of additional phosgene; and the final solution of reaction products is fractionated to recover hydrogen chloride, unreacted phosgene, and solvent for recycling, isocyanate product, and distillation residue. Although higher isomer content MDI may be produced from a high diamine-content product, most producers obtain it by distillation tapping of an amine or isocyanate from an amine that has been produced to provide both diisocyanate and polymeric isocyanate. In any case after distillation, the products of the synthesis are cooled. Although mixtures of polymeric isocyanates dimerize less rapidly than MDI alone, slow cooling of either can result in the dimer content exceeding its solubility in the isocyanate, usually one percent. In the present invention, isomeric MDI is added in calculated amounts to polymeric MDI having a 2 ring content of between 40 to 50 percent by weight. These blends within the limitations given are stable for up to six months at 25° C. and unexpectedly exhibit viscosities of between 15 and 37 cps at 25° C.

Having thus described the invention, the following examples are meant as illustration:

ISO A is a polymethylene polyphenylpolyisocyanate having a functionality of 2.7 and an NCO content of 31 percent by weight. It has a viscosity of 200 centipoise at 25° C. It further has a ring distribution of 43.5 percent by weight 4,4'-MDI; 2.7 percent by weight 2,4'-MDI; 20 percent by weight 3-ring MDI; and 33.8 percent by weight 4-ring and greater oligomers.

ISO B is an isomeric diphenylmethane diisocyanate mixture having a functionality of 2.0, is liquid at room temperature, and has an NCO content of 33.5 percent by weight. It has an isomer distribution of 49 percent by weight 4,4'-MDI; 50 percent by weight 2,4'-MDI; and 1 percent by weight 2,2'-MDI.

ISO C is an isomeric diphenylmethane diisocyanate mixture having a functionality of 2.0, a melting point at 38° C., and an NCO content of 33.5 percent by weight. It has an isomer distribution of 98 percent by weight 4,4'-MDI and 2 percent by weight 2,4-MDI.

The following procedure was used to prepare all blend samples. Calculated amounts of the liquid isocyanates A and B (Example 1 in Table 1 contain 45 percent and 10 percent by weight, respectively) were charged to a clean, dry reaction vessel which had been previously purged with nitrogen. The contents of the vessel were subject to agitation and a nitrogen blanket throughout the operation. The contents of the vessel were heated to 45° C. to 50° C. A calculated amount of molten Iso C (in Example 1, 45 percent by weight) was then added to the reaction vessel. The blend was agitated at 45° C. to 50° C. for 30 minutes. The blend was then tested for specific properties.

Table 1 shows the ring distribution for various blends of Isos A, B and C, the total NCO content, and viscosities. Examples 1-4 serve to illustrate the invention. Blends having up to 78.4 percent by weight (Ex. 4) 2-ring content of which 93.8 percent by weight is the 4,4'-isomer are stable and exhibit low viscosities. Examples 5-7 (2-ring greater than 80 percent by weight), on the other hand, were not stable. In order to stabilize the blends, greater amounts of the 2,4-isomer (>10 percent by weight) were added (Ex. 8-10).

TABLE 1

| EX. | 4,4'-/** | 2,4'-/* | 2 RING | 3 RING | OLIGO. | NCO | VISC. |
|---|---|---|---|---|---|---|---|
| 1 | 68.6/ 90.6 | 7.1/ 9.4 | 75.7 | 9.0 | 15.3 | 32.66 | 26 |
| 2 | 63.1/ 89.8 | 7.2/ 10.2 | 70.3 | 11.0 | 18.7 | 32.44 | 37 |
| 3 | 71.0/ 93.8 | 4.7/ 6.2 | 75.7 | 9.0 | 15.3 | 32.65 | 28 |
| 4 | 72.0/ 92.0 | 6.4/ 8.0 | 78.4 | 8.0 | 13.6 | 32.66 | 24 |
| 5 | 74.0/ 91.3 | 7.1/ 8.7 | 81.1 | 7.0 | 11.9 | 32.87 | MS |
| 6 | 76.8/ 91.7 | 7.0/ 8.3 | 83.8 | 6.0 | 10.2 | 32.97 | MS |
| 7 | 77.1/ 89.1 | 9.4/ 10.9 | 86.5 | 5.0 | 8.5 | 33.08 | MS |
| 8 | 71.6/ 88.3 | 9.5/ 11.7 | 81.1 | 7.0 | 11.9 | 32.87 | 24 |
| 9 | 72.0/ 85.1 | 11.8/ 14.1 | 83.8 | 6.0 | 10.2 | 32.97 | 22 |
| 10 | 72.3/ 83.6 | 14.2/ 16.4 | 86.5 | 5.0 | 8.5 | 33.08 | 20 |

All values in the table are given in weight percent. Except for the viscosity, all the other values are calculated.
*2,4'-MDI weight percent of total 2 ring in the blend. Oligo.: higher than 3 ring.
MS = marginally stable at temperatures of 23° C. to 27° C. while those with the viscosity numbers displayed excellent stability.
**4,4'-MDI weight percent of total 2 ring in the blend.

What is claimed is:

1. A process for the preparation of storage stable polyisocyanate blends having viscosities from 15 cps and 37 cps at 25° C., comprising the steps of mixing:
   A. a polymethylene polyphenylpolyisocyanate with,
   B. diphenylmethane diisocyanates,
wherein the ring distribution based on the total weight of the blend is,
   1) about 60 percent to about 75 percent by weight 4,4'-diphenylmethane diisocyanate,
   2) about 4 percent to about 10 percent by weight 2,4'-diphenylmethane diisocyanate,
   3) less than 1 percent by weight 2,2'-diphenylmethane diisocyanate,
   4) about 8 percent to about 15 percent by weight of a 3-ring polymethylene polyphenylpolyisocyanate, and,
   5) about 5 percent to about 15 percent by weight of 4-ring and higher oligomeric polymethylene polyphenylpolyisocyanate,
and the sum of the 4,4'- and 2,4'-diphenylmethane diisocyanate does not exceed 80 percent by weight of the total blend.

2. A storage stable polyisocyanate blend, comprising:
   A. a polymethylene polyphenylpolyisocyanate, and,
   B. a diphenylmethane diisocyanate,
wherein said blend has a viscosity of from 15 cps to 37 cps at 25° C., and a ring distribution of,
   i) about 60 percent to about 75 percent by weight 4,4'-diphenylmethane diisocyanate,
   ii) about 4 percent to about 10 percent by weight 2,4'-diphenylmethane diisocyanate,
   iii) less than 1 percent by weight 2,2'-diphenylmethane diisocyanate,
   iv) about 8 percent to about 12 percent by weight of a 3-ring polymethylene polyphenylpolyisocyanate, and,
   v) about 5 percent to about 15 percent by weight of 4-ring and higher oligomeric polymethylene polyphenylpolyisocyanate,
wherein the sum of the 4,4'- and 2,4'-diphenylmethane diisocyanate does not exceed 80 percent by weight of the total blend.

3. A process as claimed in claim 1, wherein the polymethylene polyphenylpolyisocyanate has an initial ring distribution of:
   A. 40 to about 50 percent by weight 2-ring isomer, wherein approximately 95 percent by weight is 4,4'-diphenylmethane diisocyanate and 5 percent by weight is 2,4'-diphenylmethane diisocyanate,
   B. 19 to about 25 percent by weight 3-ring polymethylene polyphenylpolyisocyanate, and
   C. 25 to 41 percent by weight 4-ring and greater oligomers of polymethylene polyphenylpolyisocyanate.

4. A process as claimed in claim 1, wherein about 10 percent by weight of a diphenylmethane diisocyanate isomer mixture consisting of about a 1:1 mixture of 2,4'- and 4,4'-diphenylmethane diisocyanate, which is a liquid at room temperature, is mixed with the polymethylene polyphenylpolyisocyanate prior to adding a molten diphenylmethane diisocyanate having a 4,4'-diphenylmethane diisocyanate content of at least 95 percent by weight.

5. A storage stable polyisocyanate blend as claimed in claim 2, comprising:
   A. 68.6 percent by weight 4,4'-diphenylmethane diisocyanate,
   B. 7.1 percent by weight 2,4'-diphenylmethane diisocyanate,
   C. 9.0 percent by weight 3-ring polymethylene polyphenylpolyisocyanate, and,
   D. 15.3 percent by weight 4-ring and greater oligomers of polymethylene polyphenylpolyisocyanate.

* * * * *